United States Patent [19]
Addey et al.

[11] Patent Number: 5,502,163
[45] Date of Patent: Mar. 26, 1996

[54] CONTROL OF SECRETION OF MILK

[75] Inventors: Caroline V. P. Addey, Ayr; Malcolm Peaker; Colin J. Wilde, both of Alloway, all of Scotland

[73] Assignee: British Technology Group Limited, London, England

[21] Appl. No.: 395,535

[22] Filed: Feb. 28, 1995

Related U.S. Application Data

[63] Continuation of Ser. No. 856,206, Jul. 13, 1992, abandoned.

[30]   Foreign Application Priority Data

Nov. 13, 1989 [GB]  United Kingdom .................. 8925595

[51] Int. Cl.$^6$ ............................ C07K 16/18; C07K 14/47
[52] U.S. Cl. ........................ 530/300; 530/344; 530/350; 530/360; 530/832; 530/833; 530/388.24; 530/417; 530/387.1
[58] Field of Search ...................... 530/300, 344, 530/350, 360, 832, 833, 388.24, 417, 387.1

[56]   References Cited

PUBLICATIONS

Prentice et al., Biochemical Society Transaction Apr. 24, 1989. p. 122.
Guiding Monoclonal Antibodies: Principles and Practice 1986.
Wilde, C. J. et al., Biochem Biophys Acta (Netherlands) Sep. 15, 1989, 992 (3) pp. 315–319.
Wilde, C. J. et al., O. J. Exp. Physiol. (England) May 1988, 73 (3) pp. 391–397.
Manji, B. et al., J. Dairy Sci., Dec. 1985, 68 (12) pp. 3176–3179.
Hill, A. R. et al., Canadian Institute of Food Science and Technology Journal, Dec. 1986 v. 19 (5) pp. 227–230.
Butler, W. R. et al., J. Dairy Sci. (United States) Mar. 1989, 72 (3) pp. 767–783.

*Primary Examiner*—Lila Feisee
*Attorney, Agent, or Firm*—Nixon & Vanderhye

[57]   ABSTRACT

A protein which inhibits milk secretion by lactating cows and which is present in the second (2A) significant peak when a nominally 10–30 KDa fraction of the whey proteins of the milk is resolved on a "Mono Q" anion exchange column using 10 mM imidazole buffer, pH 7.0 and a sodium chloride elution gradient. Its pI by isoelectric focussing in a gel tube is 4.8 to 5.0.

2 Claims, 3 Drawing Sheets

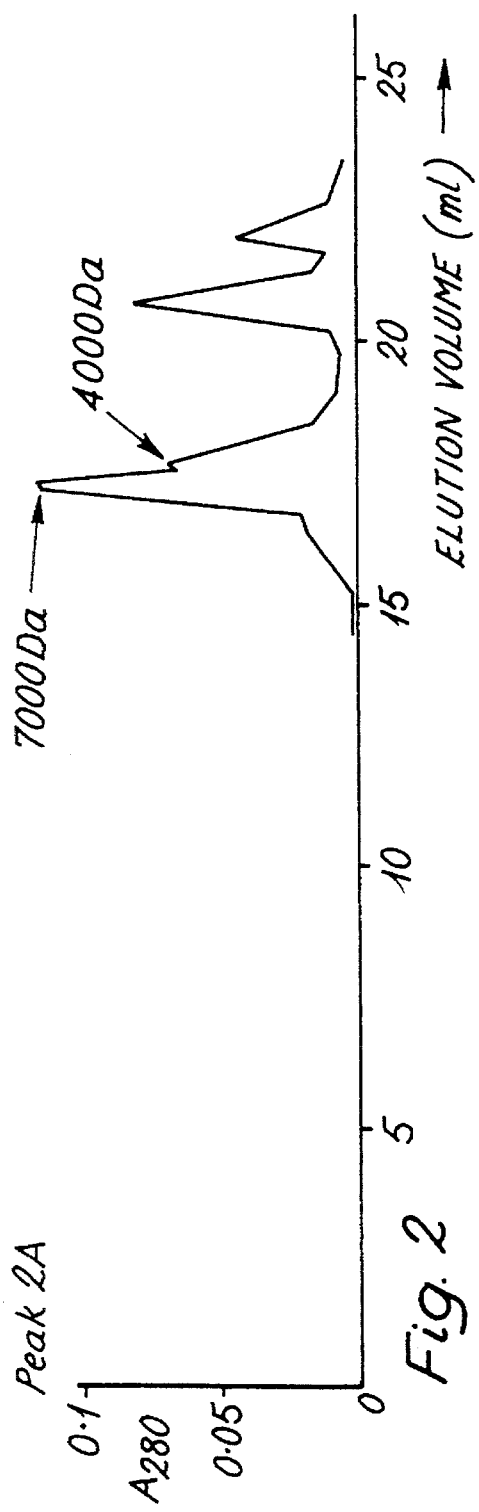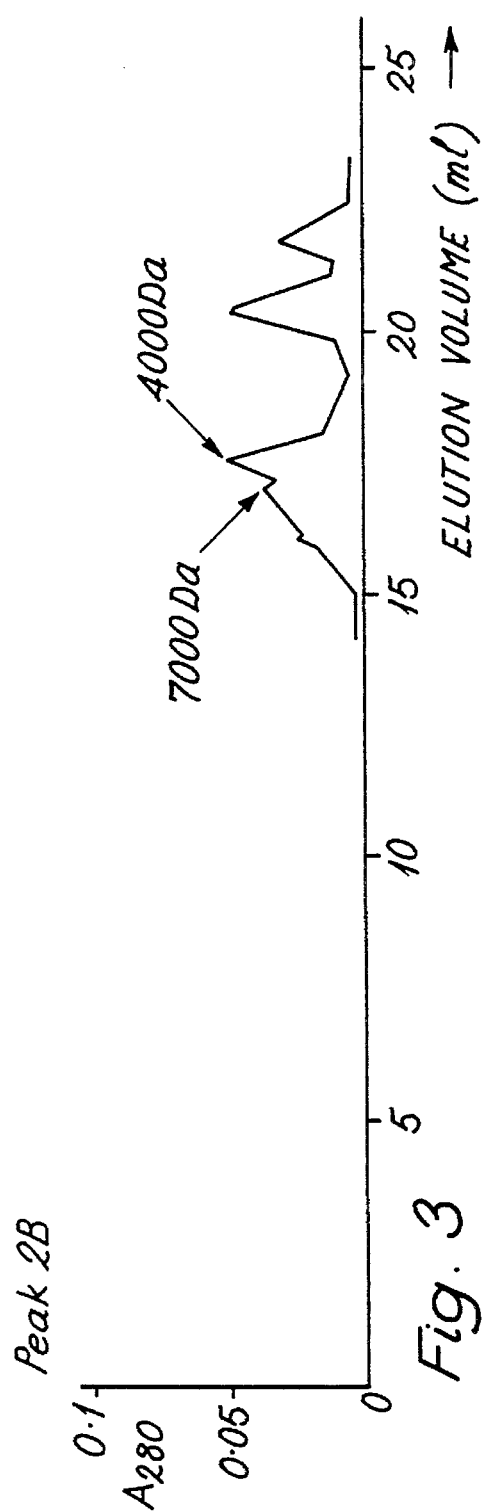

CONTROL OF SECRETION OF MILK

This is a Rule 62 continuation of patent application Ser. No. 07/856,206, filed 13 Jul. 1992, now abandoned.

BACKGROUND OF THE INVENTION

1. Field of the Invention

This invention relates to a newly isolated protein from cow's milk and the use of the protein or antibodies thereto for the control of milk secretion in lactating animals.

2. Description of the Prior Art

The rate of milk secretion by a lactating animal is regulated by the frequency of milk removal. In other words, there is a mechanism which acts to match the animal's supply of milk to the demand of her offspring or of a farmer's milking regime. Part of this control is achieved by the release of galactopoietic hormones during suckling or milking. However, studies by workers at the Hannah Research Institute, Ayr, Scotland on lactating goats have shown that another factor is involved. This is an inhibitor which decreases milk secretion at a local level, i.e. at the individual gland of an udder.

It has already been shown that the inhibitor is present in a goat milk fraction containing whey proteins of molecular weight 10–30 KDa, this range of molecular weights being determined by the nominal sizes of filters used in ultrafiltration of the whey. The effect has been demonstrated both LB vitro and in vivo. The in vitro technique, described by C. J. Wilde et al., Biochem. J. 242, 285–288 (1987), consists in culturing explanted pieces of rabbit mammary with and without the milk fraction and demonstrating the inhibition of lactose and casein synthesis. See also G. M. Stewart et al.. *J. Endocrinology* 118, R1 –R3 (1988). In the in vivo technique. C. J. Wilde et al., *Quarterly Journal of Experimental Physiology* 73, 391–397 (1988), the milk fraction was injected into a single mammary gland of goats via the teat canal. A temporary dose-dependent reduction of milk yield, specific to that gland, was observed.

It has remained a problem to determine whether an inhibitor is present in cow's milk and, if so, to purify it sufficiently for identification, with a view to chemical or biological synthesis.

SUMMARY OF THE INVENTION

It has now been found that inhibitory activity is present In a 10–30 KDa fraction of whey from cow's milk, that this fraction can be separated by anion exchange FPLC (Fast Protein Liquid Chromatography) into a number of peaks and that the inhibitory activity is concentrated mainly in two particular peaks out of eight.

There are various ways of defining the protein of the invention, of varying degrees of reliability. One currently preferred definition is a protein which inhibits milk secretion by lactating cows and which is present in the second significant peak (labelled "2A" in FIG. 1) when a nominally 10– 30 KDa fraction of the whey proteins of the milk is resolved on an anion exchange column containing particles of monodisperse hydrophilic polymers having pendent $—CH_2N(CH_3)_{3+}$ groups, the particle diameter being $10\pm0.5$ µm, especially a "Mono Q" column, using 10 mM imidazole buffer, pH 7.0 and a sodium chloride elution gradient.

The molecular weight of the peak 2A protein as determined by gel filtration chromatography is about 7 KDa. When the peak 2A protein is further resolved, by gel filtration chromatography on a cross-linked agarose gel having a particle size of $10\pm2$ µm, such as "Superose", the major component, which is that which appears second, comprises the inhibitory protein. Further when peak 2A (or its equivalent in which the whey is not fractionated before anion exchange chromatography) is resolved on a chromatofocussing column containing particles of monodisperse hydrophilic polymers having pendant tertiary ($—N^+HR_2$) and quaternary ($—N^+R_3$) amine groups where R represents an organic group, the particle diameter being $10\pm0.5$ µm, especially a "Mono P" column, using 10 mM imidazole, pH 6.5 and amphoteric buffer of pH 4.0 to create a pH gradient of 6.5–4.0, the protein is present in the second significant peak ("2A.2").

Any combination of one or more of the above features, together with the inhibitory action of the protein, might be sufficient to define the protein uniquely and accordingly applicant does not wish to be limited unnecessarily to specific combinations, in case one of them or some aspect of one of them might later be re-determined and found not sufficiently to approximate to their definition given above, while the remaining features are confirmed, and leave no doubt as to the identity of the protein. Precisely which features are the most meaningful and the most reliable are. In any case, a matter of judgement, the preferred definitions given above reflecting applicant's current judgement. It will be appreciated, therefore, that the protein defined by other combinations of features herein set forth is to be considered as encompassed by the invention.

A property which might be useful for defining the protein is the isoelectric point (pI). It has been found that peak 2A gives a pI in the range 4.8 to 5.0 when determined in a tube of polyacrylamide gel, while peak 2A.2 gives a pI of 4.9–5.0 determined by isoelectric focussing.

The protein can be in glycosylated or unglycosylated form.

Antibodies to the protein, whether polyclonal, monoclonal or engineered, are within the scope of this invention.

Where national patent law permits, the administration of the inhibitor to decrease milk yield or an antibody thereto to suppress at least partly the action of the inhibitor, to cows or other animals is within the invention.

BRIEF DESCRIPTION OF THE DRAWINGS

FIGS. 2 and 3 show the further resolution of two of the peaks of the FIG. 1 anion exchange chromatography by gel filtration chromatography.

DESCRIPTION OF THE PREFERRED EMBODIMENTS

Figure 1:
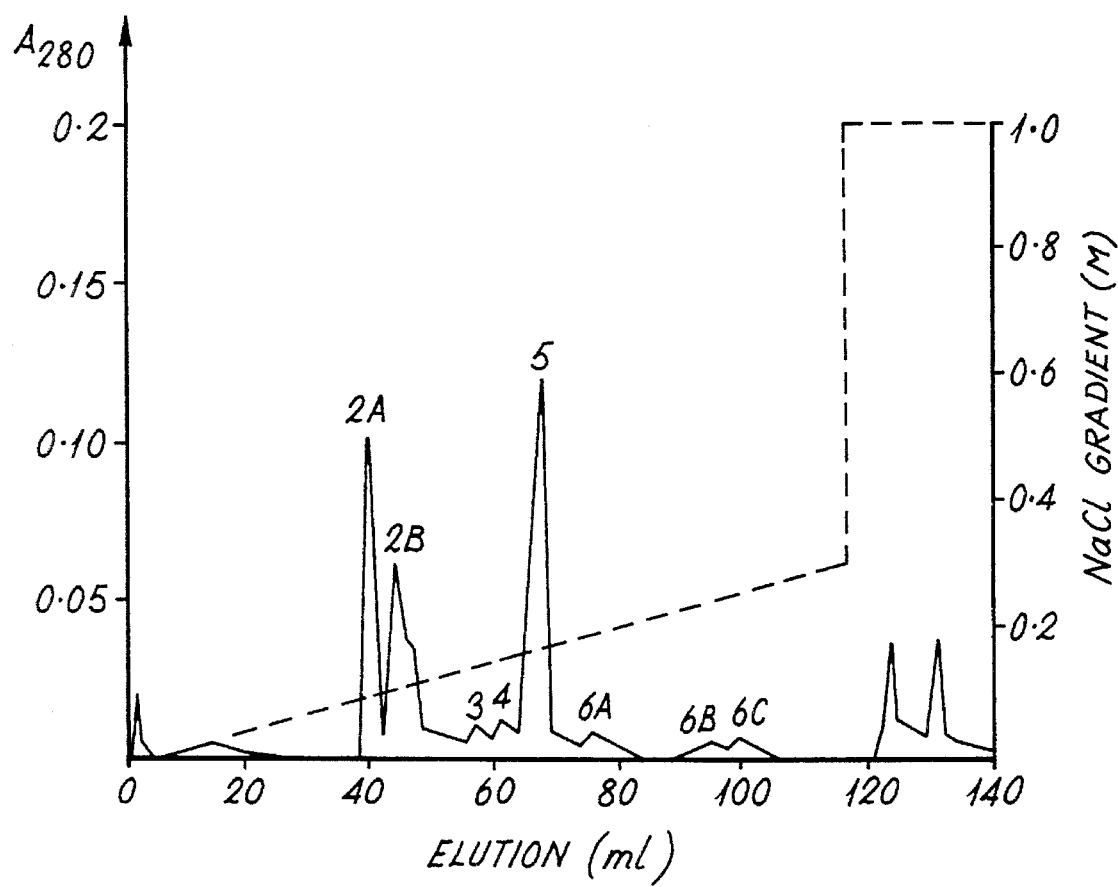
FIG. 1 shows the resolution of the 10–30 KDa fraction by anion-exchange chromatography.

The protein of the invention exists in cow's milk, probably in glycosylated form. It is believed that the effect of glycosylation is simply for attachment of the protein to the appropriate cells within the mammary gland. It would be expected, therefore, that the protein could be administered locally to the gland in an unglycosylated form.

In relation to goat's milk, using a 10–30 KDa fraction of whey protein, it has been demonstrated that the inhibition of lactose and casein synthesis in mammary explant culture is dependent on the dose of the inhibitor-containing fraction. Further, when the explants have been exposed to the inhibitor-containing fraction, washed and re-cultured in fresh medium in the absence of the inhibitor, the capacity to synthesise lactose and casein is recovered. In vivo, it is found that administration of the protein to the mammary gland causes the milk yield to decrease within hours, with full recovery of yield 24–36 h after a single administration. However, when a change in milking frequency—and therefore autocrine control— was sustained over weeks, there was an effect on the synthetic capacity i.e. degree of differentiation of the secretory cells attributable to the autocrine inhibitor. These long-term effects on mammary cell activity are accompanied by changes in the number of cell-surface hormone receptors for prolactin. Thrice-daily milking of lactating goats for 4 weeks increases cell activity and prolactin receptor number per cell, whereas a decrease in milking efficiency extending over 21 weeks reduces secretory cell differentiation and prolactin receptor number. Therefore, these long-term effects, and also the acute regulation by the autocrine inhibitor of the invention could be due primarily to modulation of the sensitivity of individual glands to endocrine control. There is every reason to believe that the same effects will be demonstrable in relation to the protein of the invention obtained from cow's milk, in relation to cows.

Antibodies can be raised against the protein of the invention by any conventional methods, e.g. as polyclonal antisera, mouse monoclonal antibodies, cow-mouse hybrid monoclonal antibodies or as engineered antibodies, by any of the currently available methods. Passive immunisation methods can then be used to generate a reduction in the effect of the natural inhibitor, when this is desired in order to increase milk yield. Frequently, however, there will be a need to reduce milk yield in order to meet milk quotas, in which event the inhibitor itself is administered. Conventional carriers and adjuvants known in vaccination can be used.

The invention is applicable to any animal responsive to the inhibitor defined herein. Since the 10–30 KDa goat's milk fraction has been successfully found to reduce milk accumulation and relevant enzyme activities when injected into the mammary gland of rabbits, it is likely that the cow's milk inhibitor will be effective in some other lactating animals.

For intraductal injection into the mammary gland, a dose in the range of 1 to 50 μg, especially 5 to 20 μg of inhibitor, is likely to be effective and should be repeated as required, e.g. daily, and possibly reduced when given over long periods.

The protein of the invention can be obtained from cow's milk by the method described in the Example or some variant thereof. It can be recovered in pure form from an eluate by extensive dialysis against water (using an appropriate membrane for retention of the protein, e.g. with a nominal molecular weight cut-off of about 6 KDa) and freeze-drying. However, it is expected that it would be synthesised by protein synthesis or by a recombinant DNA method.

The following Example illustrates the invention.

EXAMPLE

This Example describes the preparation and properties of the inhibitor of the invention.

1. Preparation of cow milk fractions

Milk was obtained at the morning milking from Friesian cows. and was defatted by centrifugation (2500 g, 15° C., 20 min) and filtered through glass wool. Defatted milk was centrifuged (80,000 g, 15° C., 2 h), yielding a pellet of casein micelles and a clear supernatant containing whey proteins. The whey fraction was dialysed against distilled water for 24 h.

The whey fraction was subjected to ultrafiltration using a filter with a nominal cut-off value of molecular weight 30,000 Daltons (Da). The filtrate obtained with the 30,000 Da filter was concentrated by ultrafiltration with a 10,000 Da filter. The 10,000–30,000 Da fraction was dialysed extensively against water, sterilized by filter sterilization and concentrated by freeze-drying for anion exchange chromatography.

2. Anion exchange chromatography of cow whey proteins

The 10–30 KDa whey fraction was resolved on a "Mono Q HR 10/10" anion exchange column (Pharmacia) using an "FPLC" chromatography system (Pharmacia). The whey fraction was dissolved in 10 mM imidazole at four times its concentration in the original milk and the pH adjusted to 7.0. Before chromatography, the sample and buffer (degassed) were filtered through 0.2 μm filters. 1 ml of the 4× concentrated whey fraction was loaded for each separation; the flow rate was 4.0 ml/min. A sodium chloride elution gradient was used.

Fractions containing protein peaks eluted from the column were dialysed extensively against distilled water, freeze-dried and stored at −20° C., before use in the next stage.

FIG. 1 of the drawings shows the elution of protein from the chromatography column. Protein concentration, as absorption of light at 280 nm, on the left-hand ordinate is plotted against cumulative volume of eluted material on the abscissa. The plot is shown as lines. The right-hand ordinate is calibrated to show the sodium chloride gradient, from 0 to 1.0 M, used in the eluant. The broken line is a plot of the sodium chloride concentration. The peaks are labelled $V_o$=void volume containing material not bound by the column and then in order of elution, the peaks being numbered as far as possible by a system which relates them to those obtained when the non-ultrafiltered whey protein is chromatographed by the same method. The numbering is 1, 2A, 2B 3, 4, 5, 6A, 6B, 6C, 7 and 8 (although the last two peaks do not correlate with those for the non-ultrafiltered whey).

3. Mammary explant bioassay of milk fractions

Mammary tissue was cultured as explants, small pieces of parenchymal tissue approximately 1 cm³ and weighing 0.5–0.7 mg. Explants were prepared from mammary tissue of mid-pregnant New Zealand White rabbits as described by R. Dils & I. A. Forsyth in *Methods in Enzymology* 72, 724–742 (1981). The explants were cultured in a defined culture medium (Medium 199: Gibco Europe Ltd., Paisley, UK) on stainless steel grids each holding 30 explants, so that the explants were in contact with the medium but not completely submerged in it. The medium was supplemented throughout with insulin (5 μg/ml), cortisol (100 ng/ml) and prolactin (1 μg/ml). Explants were cultured in this medium under an atmosphere of air/$CO_2$ (19:1 v/v) for 42 h, with replenishment of medium after 24 h. At this time, groups of explants (3 or 4 groups per treatment) were transferred into fresh medium containing hormones and one of the fractions of cow milk under test. The milk fractions tested in this experiment were obtained from cow's milk whey which had not been ultrafiltered (as distinct from the 10–30 KDa fraction referred to above), but which had been fractionated by anion exchange chromatography as described above. They were dissolved in 10 mM Hepes, pH 7.4, at twice their concentration in the original milk, and added to an equal volume of two times concentrated culture medium, so as to be at 100% of their original milk concentration in normal strength culture medium. Control cultures, containing only the diluent for the milk fractions, were included in each experiment. Average rates of lactose and casein synthesis during a further 6 h culture in the presence or absence of milk fraction were measured by the addition of [U-$^{14}$C] glucose (U= uniformly labelled: 0.18 mCi/mmol) and L-[4.5-$^3$H]leucine (2.22 mCi/mmol) respectively in this culture medium. At the end of the 6 h period, explants and culture medium were separated and stored frozen in liquid nitrogen.

Explants were homogenized at 4° C. in 1.0 ml of 10 mM Tris/HCl. pH 7.0, containing 5 mM ethyleneglycol-bis-(2-aminoethyl ether) N,N,N',N'-tetraacetic acid (EGTA) and 2 mM phenylmethanesulphonyl fluoride by 10 strokes with a glass/PTFE homogenizer, followed by sonication for 30s (Kontes ultrasonic cell disruptor, 30% maximum power), and a particle-free supernatant was prepared by centrifugation at 10,000 g for 5 min. $^3$H-labelled casein was prepared from the particle-free supernatant by precipitation at its isoelectric point, and the precipitate was subjected to SDS-polyacrylamide gel electrophoresis, as described by C. J. Wilde et al., Exp. Cell Res. 151, 519–532 (1984). Bands corresponding to casein polypeptides were visualized by staining with Coomassie brilliant blue, and were excised and counted for [$^3$H] radioactivity as described by S. M. Russell et al., Biochim. Biophys. Acta 714, 34–45 (1982). [$^{14}$C] lactose was selectively precipitated from explant homogenates and culture medium using ethanol/diethyl ether (3:1, v/v), N. J. Kuhn & A. White, Biochem. J. 148, 77–84 (1975) and the radioactivity of the precipitate counted. Results were corrected for carry-through of [$^{14}$C] glucose from culture medium (usually <0.08%), by measuring [$^{14}$C] radioactivity after extraction of uncultured medium. The addition of milk fractions did not affect the distribution of secreted products between the extracellular space of the explants and the medium.

The amount of radioactive material (casein and lactose) was expressed as a percentage of that produced by the explants to which no milk fraction had been added. The results are shown in Table 1. The figures in parenthesis are the numbers of experiments performed on various peaks.

TABLE 1

| Peak number | Lactose synthesis (% of control) | Casein synthesis (% of control) |
|---|---|---|
| No addition (control) | 100 | 100 |
| 1 | 96.8 ± 3.7 (5) | 90.6 ± 3.5 (5) |
| 2(= 2A + 2B) | 65.8 ± 7.5 (6)* | 63.1 ± 14.2 (6)* |
| 3 | 94.6 ± 4.6 (5) | 86.7 ± 12.2 (5) |
| 4 | 104.0 ± 6.0 (5) | 146.4 ± 22.8 (5) |
| 5 | 102.1 ± 1.7 (4) | 94.3 ± 21.3 (5) |
| 7 | 85.3 ± 9.8 (4) | 91.6 ± 19.8 (5) |
| 8 | 90.4 ± 4.8 (3) | 94.4 ± 6.1 (5) |
| 9 | 110.9 ± 5.6 (3) | 90.3 ± 10.8 (4) |
| 10 | 102.0(2) | 120.3(2) |

*Test vs control; p < 0.05 (paried t-test)?

From the Table it will be seen that peak 2 was the more active than the others in inhibiting lactose synthesis, a major determinant of milk yield, and casein synthesis.

The above experiments were then repeated, using fractions from peaks 2A and 2B, with the results shown in Table 2 below.

TABLE 2

| Peak number | Lactose synthesis (% of controls) | Casein synthesis (% of controls) |
|---|---|---|
| No addition (control) | 100 | 100 |
| 2A | 71.4 ± 9.1 | 53.9 ± 5.9 |
| 2B | 80.9 ± 9.6 | 80.8 ± 6.6 |

Results are the mean ± s.e.m. for 3 experiments.

It will be seen that both fractions were inhibitory to some extent, although lack of clear separation of the inhibitor component between peaks 2A and 2B accounts for some of these effects.

4. Gel filtration chromatogranhy of peaks

Gel filtration of each of peaks 2A and 2B prepared from the 10–30 KDa fraction as described above was carried out using an "FPLC" chromatography system and a "SUPEROSE 12 HR 10/30" column (Pharmacia). "SUPEROSE 12" is a highly cross-linked agarose matrix with a particle size of 10±2 μm and an exclusion limit of 2×10$^6$ Da. The buffer was 50 mM Tris/HCl, pH 7.5 containing 100 mM KCl, which was filtered (0.2 μm filter) and degassed before use. Samples (routinely 1–10 μg in a maximum volume of 200 μl) were dissolved in the same buffer and filtered before use (0.2 μm filter). The column was calibrated using molecular weight standards in the m.w. range 200,000–12,400 (Sigma MW-GF-200 kit) and also aprotinin (molecular weight 6,500) and bovine α-lactalbumin (molecular weight 14,200). Calibration curves of log[molecular weight] versus $V_e/V_o$ were prepared, where $V_o$=void volume and $V_e$=elution volume of each protein. $V_o$ was determined using Dextran Blue (Sigma; approximate molecular weight 2,000 KDa). FIGS. 2 and 3 show the results of the gel filtration, protein absorption at 280 nm on the ordinate being plotted against elution volume on the abscissa. It will be seen from FIG. 2 that peak 2A is resolved into three separated peaks and a shoulder downstream of the first main peak. The components of m.w. 7 and 4 KDa were assigned to the first main peak and its shoulder respectively. The 7 KDa component is clearly the main one of peak 2A. Peak 2B was resolved into three separated peaks and a shoulder upstream of the main peak, the components of m.w. 7 and 4 KDa being assigned to the shoulder and main peak respectively. The molecular weights of the principal components were determined to be about 7 and 4 KDa. (An attempt at m.w. determination by SDS-PAGE gave anomalous results: it appears that high molecular weight aggregates form). The unexpectedly low molecular weights can probably be explained by clogging of the nominally 10,000 Dalton filter during ultrafiltration, allowing smaller molecules to be retained.

5. Isoelectric focussing of cow whey proteins

Isoelectric focussing was performed in tube gels (diameter, 4 mm; length 11.5 cm). 4% polyacrylamide gels were prepared essentially as described by P. H. O'Farrell, J. Biol. Chem. 250, 4007–4021 (1975) using a mixture of ampholines (4% v/v pH range 5–8; 1% v/v pH range 3.5–10; BioRad), which gave a linear gradient in the range 4.0–9.0. Samples (25 μg of the peak 2 protein) were dissolved in a solution containing 9.5M urea, 2% (w/v) NP40, 1.6% (v/v) pH 5–8 ampholines and 0.4% (v/v) pH 3.5–10 ampholines. The anodic and cathodic solutions were 10 mM H$_3$PO$_4$ and 20 mM NaOH respectively. Electrophoresis was at 300 V for 18 h, followed by 400 V for 4 h. Gels were extruded and fixed first in 25% (v/v) isopropanol/10% (v/v) acetic acid, then in 5% (w/v) TCA/5% (w/v) sulphosalicylic acid/1%

(v/v) methanol, and were stained 25% (v/v) isopropanol/ 10% (v/v) acetic acid containing 0.1% (w/v) Coomassie Blue. Destaining was in isopropanol/acetic acid.

Two bands were obtained. The major band has an isoelectric point of 4.84; the minor band focusses at an isoelectric point of 4.92.

6. Separation of peak 2A components by chromatofocussing

Chromatofocussing separates proteins on the basis of their isoelectric point (pI). Resolution with the Pharmacia "Mono P HR 5/20" column is such that molecules differing in pI by only 0.02 pH units can be separated. "MONO P" is a weak anion exchanger, based on monobeads, i.e. monodisperse hydrophilic polymer particles (10±0.5 μm diameter) into which various tertiary (—$N^+HR_2$) and quaternary (—$N^+R_3$) amine groups are introduced. "Mono P" has a buffering capacity and the amount of charge it carries will vary with pH. Consequently, its ionic capacity will also vary with pH. In chromatofocussing, a pH gradient is formed on the column by equilibrating it with start buffer and eluting with another buffer which is added in increasing amounts, thereby adjusting the solution progressively to a lower pH. Proteins bound to the column at the starting pH are eluted at different points on the pH gradient according to their pI.

A "MONO P" column was pre-washed with 1 ml of 1M NaOH, and the equilibrated in 10 mM imidazole, pH 6.5. The sample, 50 μg of ultrafiltered bovine whey protein, peak 2A, obtained by anion-exchange chromatography as described in section 2 of this Example, was applied once the pH of the column eluant had returned to 6.5. The column was eluted with a 1/10 v/v dilution of "POLYBUFFER" 74, pH 4.0 in distilled water. "POLYBUFFER" (Pharmacia) contains numerous amphoteric buffering substances of different pKa. Buffers were filtered through 0.2 μm filters and degassed before use. Elution was carried out at a flow rate of 0.5 ml/min, until the pH of the eluant was 4.5. Protein eluting from the column was detected by monitoring absorbance of the eluant at 280 nm.

Figure 4:
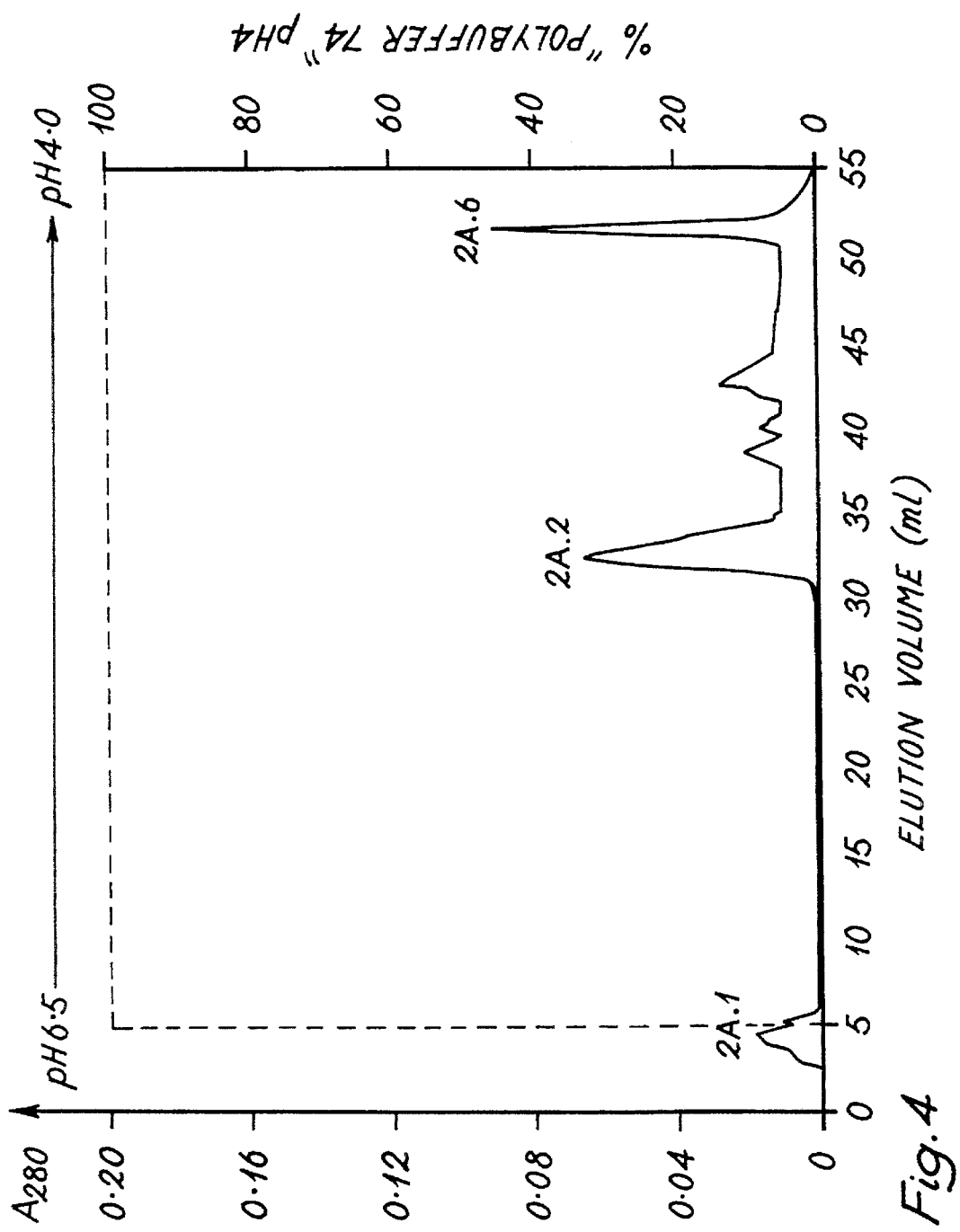
FIG. 4 shows the further resolution of one of the peaks obtained from anion-exchange chromatography by chromatofocussing.

Peak 2A eluted as three major (2A.1, 2A.2 and 2A.6) and three minor peaks (2A.3, 2A.4 and 2A.5) as shown in FIG. 4. The relative abundance of these components varies between separations. However, the separation is qualitatively reproducible in terms of the relative positions of the peaks. The second major peak Peak 2A.2 which elutes at pH 5.0–4.9 is that which predominantly contains the inhibitor (see section 7 below).

7. Mammary explant bioassay of chromatofocussed peaks

The bioassays were carried out as described in section 3. The samples tested in this experiment had been fractionated by chromatofocussing of ion-exchange peak 2A as described in section 5. They were dissolved in 10 mM Hepes. pH 7.4, at twice their concentration in the original milk and added to an equal volume of twice concentrated culture medium so as to be at 100% of their original milk concentration in normal strength culture medium. Control cultures containing only the milk fraction diluent were included in each experiment. Average rates of lactose and caesin synthesis were measured as described previously (section 3).

The amount of radioactive material was expressed as a percentage of that produced by the explants to which no milk fraction was added. The results are shown in Table 3 below. The figures in parenthesis are the numbers of experiments performed on the various peaks. Results are the mean±s.e.m. where three experiments were carried out.

TABLE 3

| Peak Number | Lactose Synthesis (% of control) | Caesin Synthesis (% of control) |
|---|---|---|
| No addition (control) | 100 | 100 |
| 2A.1 | 142 (1) | 107 (1) |
| 2A.2 | 66.8 ± 11.1 (3) | 67.0 ± 19.5 (3) |
| 2A.6 | 101.5 (2) | 102.9 (2) |

From the above table it can be seen that of the fractions tested only Peak 2A.2 was inhibitory.

8. Gel-filtration chromatography of Peak 2A.2

Gel-filtration of peak 2A.2 (section 7) was carried out using an FPLC chromatography system and a SUPEROSE 12 HR 10/30" column (Pharmacia), as described in section 4 for the anion-exchange peaks. Peak 2A.2 eluted as the sole protein-containing peak. The other peaks contained no detectable protein and were of low molecular weight (<1 kDa). The molecular weight of Peak 2A.2 was calculated to be about 7.0 kDa which was the molecular weight estimated for anion-exchange peak 2A in section 4.

9. Isoelectric focusing of chromatofocussed peak 2A.2

Isoelectric focusing was performed using the Pharmacia "PHASTGEL" electrophoresis system. The method used "PHASTGEL IEF 4–6.5". "PHASTGEL IEF" media are homogeneous polyacrylamide gels containing "Pharmalyte" carrier ampholytes. "Pharmalyte" generates stable, linear pH gradients in the gels during electrophoresis, in this case in the pH range 4 to 6.5. Proteins migrate under an electric field, essentially unhindered by the porous gel, to a point in the pH gradient that corresponds to their pI (isoelectric point).

The sample, 1 μg, of Peak 2A.2 (section 6) which had been extensively dialysed against distilled water was applied to one well of the gel, "Pharmacia pI Calibration Kit" proteins were applied to wells on both sides of the sample well. The resulting protein bands were visualised by staining with Coomassie blue after electrophoresis. Peak 2A.2 gave rise to a single protein band corresponding to pI 4.9–5.0.

We claim:

1. An isolated protein in glycosylated or unglycosylated form which inhibits milk secretion by lactating cows and which is present in the second significant peak ("2A") when a fraction of the whey proteins of the milk, obtained from said lactating cows separated by ultrafiltration using filters of cut-off values 10 KDa and 30 KDa, is resolved on an anion exchange column of particles of monodisperse hydrophilic polymers having pendant —$CH_2N(CH_3)_3^+$ groups, the particle diameter being 10±0.5 μm, using 10 mM imidazole buffer, pH 7.0 and a 0 to 1.0M sodium chloride elution gradient and further which is present in the second significant peak obtained when peak 2A is further resolved on a chromatofocussing column containing particles of monodisperse hydrophilic polymers having pendant tertiary —$N^+HR_2$ and quaternary —$N^+R_3$ amine groups where R represents an organic group, the particle diameter being 10±0.5 μm, using 10 mM imidazole, pH 6.5 and amphoteric buffer of pH 4.0 to create a pH gradient of 6.5 and said protein having a molecular weight as determined by gel filtration chromatography, of about 7 KDa and an isoelectric point, as determined by isoelectric focussing of material from said peak 2A in a tube of polyacrylamide gel within the range 4.8 to 5.0.

2. An antibody to a protein which inhibits milk secretion by lactating cows and which is present in the second significant peak 2A when a fraction of the whey proteins of the milk obtained from said lactating cows separated by ultrafiltration using filters of cut-off values 10 KDa and 30 KDa, is resolved on an anion exchange column of particles of monodisperse hydrophilic polymers having pendant —$CH_2N(CH_3)_3^+$ groups, the particle diameter being 10±0.5 μm, using 10 mM imidazole buffer, pH 7.0 and a 0 to 1.0M sodium chloride elution gradient and further which is present in the second significant peak obtained when peak 2A is further resolved on a chromatofocussing column containing particles of monodisperse hydrophilic polymers having pendant tertiary —$N^+HR_2$ and quaternary —$N^+R_3$ amine groups where R represents an organic group, the particle diameter being 10±0.5 μm, using 10 mM imidazole, pH 6.5 and amphoteric buffer of pH 4.0 to create a pH gradient of 6.5–4.0, and said protein having molecular weight, as determined by gel filtration chromatography, of about 7 KDa and an isoelectric point, as determined by isoelectric focussing of material from said peak 2A in a tube of polyacrylamide gel within the range 4.8 to 5.0.

\* \* \* \* \*